United States Patent [19]

Cryz et al.

[11] Patent Number: 5,370,872

[45] Date of Patent: Dec. 6, 1994

[54] *ESCHERICHIA COLI*-POLYSACCHARIDE-PROTEIN CONJUGATE VACCINE

[75] Inventors: Stanley J. Cryz, Bolligen; Emil P. Fürer, Muri, both of Switzerland

[73] Assignee: Swiss Serum and Vaccine Institute Berne, Berne, Switzerland

[21] Appl. No.: 743,787

[22] Filed: Aug. 12, 1991

[51] Int. Cl.$^5$ ................ A61K 39/116; A61K 39/385; C07K 17/10
[52] U.S. Cl. .................... 424/194.1; 424/197.11; 424/257.1; 530/395; 530/404; 530/405; 530/406; 530/411
[58] Field of Search ............... 530/395, 405, 406, 404, 530/807, 411; 424/88, 92, 87

[56] References Cited

U.S. PATENT DOCUMENTS

| | | | |
|---|---|---|---|
| 4,619,828 | 10/1986 | Gordon | 424/92 |
| 4,695,624 | 9/1987 | Marburg et al. | 530/395 |
| 4,711,779 | 12/1987 | Porro et al. | 424/92 |
| 4,771,127 | 9/1988 | Cryz et al. | 530/395 |
| 4,918,163 | 4/1990 | Young et al. | 424/87 |
| 5,034,516 | 7/1991 | Roy et al. | 536/4.1 |

FOREIGN PATENT DOCUMENTS

9013660  11/1990  WIPO ............. A61K 39/40

OTHER PUBLICATIONS

Cryz, Jr. et al. (1986) Infect Immunity 52(1):161–165.
Cryz, Jr. et al. (1990, Feb.) Infect Immunity 58(2)373–377.
Cryz, Jr. et al. (1991, May) JID 163(5): 1040–1045.
Jennings et al. (1984) Infect Immun. 43(1):407–412.
Fay et al. (1984) Infect Immunity 45(1):217–221.
Grandsden et al., "Bacteremia Due to *Escherichia coli*:A Study of 861 Episodes", Reviews of Infectious Diseases 12(6):1008–1018 (1990).
Cross et al., "The Importance of the K1 Capsule in Invasive Infections Causes by *Escherichia coli*", The Journal of Infectious Diseases 149(2):184–193 (1984).

*Primary Examiner*—Kay K. A. Kim
*Attorney, Agent, or Firm*—Bradford E. Kile; Kevin M. O'Brien; Ruffin B. Cordell

[57] ABSTRACT

The present invention relates to a method of producing an *E. coli* vaccine and to the vaccine produced thereby. The method involves purifying lipopolysaccharide from *E. coli* expressing complete O-polysaccharide side-chains; isolating the O-polysaccharide region of the lipopolysaccharide molecule by hydrolysis in dilute acetic acid and purifying it essentially free of lipid A; and covalently coupling lipid A-free O-polysaccharide via at least one hydroxyl or carboxyl group of the polysaccharide to a carrier protein. Polyvalent vaccines are prepared by combining two or more monovalent vaccines for different serotypes prepared according to the present invention. The present also relates to conjugates used in the vaccines. The conjugates of the present invention are the O-polysaccharide region of an *E. coli* lipoplysaccharide molecule covalently coupled to a carrier protein.

7 Claims, No Drawings

ESCHERICHIA COLI O-POLYSACCHARIDE-PROTEIN CONJUGATE VACCINE

BACKGROUND OF THE INVENTION

1. Field of the Invention

The present invention is directed to a method of producing a vaccine effective against one or more *Escherichia coli* (*E. coli*) strains. The present invention futher relates to a polyvalent vaccine composed of nonpyrogenic, nontoxic, immunogenic serotype-specific LPS based conjugates and to the conjugates therein.

2. Description of the Art

*Escherichia coli* (*E. coli*) is the leading cause of life-threatening gram-negative bacterial sepsis. Both capsular (K) and lipopolysaccharide (LPS) (O) antigens are important virulence factors as described in Cross, A. S., Kim, K. S., Wright, D. C., Sadoff, J. C., Gemski, P., "Role of lipopolysaccharide and capsule in the serum resistance of bacteremic strains of *Escherichia coli*," J. Infect. Dis. 154: 497-503, 1986; and Pluschke, G., Mayden, J., Achtman, M., Levine, R. P., "Role of the capsule and O antigen in resistance of O18:K1 *Escherichia coli* to complement-mediated killing," Infect. Immun. 42: 907-913, 1983. Both capsular and LPS antigens can confer protection against the bactericidal effect of normal human serum, a characteristic which allows *E. coli* to invade and persist in the bloodstream as noted in Cross, A. S., Kim, K. S., Wright, D. C., Sadoff, J. C., Gemski, P., "Role of lipopolysaccharide and capsule in the serum resistance of bacteremic strains of *Escherichia coli*," J Infect. Dis. 154: 497-503, 1986; and Pluschke, G., Mayden, J., Achtman, M., Levine, R. P., "Role of the capsule and O antigen in resistance of O18:K1 *Escherichia coli* to complement-mediated killing," Infect. Immun. 42: 907-913, 1983.

Serospecific antibodies directed against either the capsular or LPS antigen can afford protection against experimental *E. coli* infections in animals as described by Cross, A. S., Zollinger, W., Mandrell, R., Gemski, P., Sadoff, J. C., "Evaluation of immunotherapeutic approaches for the potential treatment of infections caused by K1-positive *Escherichia coli*," J Infect. Dis. 197: 68-76, 1983; and Kaijser, B., Ahlstedt, S., "Protective capacity of antibodies against *Escherichia coli* O and K antigens," Infect. Immun. 17: 286-289, 1977. A limited number of both O and K antigens are expressed by *E. coli* strains which cause serious infections, such as septicemia, making vaccines composed of either antigen feasible as noted in Ørskov, F, Øskov, I., "*Escherichia coli* extraintestinal infections," J. Hyg 95: 551-575, 1985; Cross, A. S., Gemski, P., Sadoff, J. C., Ørskov, F., Øskov, I., "The importance of the K1 capsule in invasive infections caused by *Escherichia coli*," J. Infect. Dis. 149: 184-193, 1984; and McCabe, W. R., Kaijser, B., Olling, S., Uwaydah, M., Hanson, L. A., "*Escherichia coli* in bacteremia: K and O antigens and serum sensitivity of strains from adults and neonates," J. Infect. Dis. 138: 33-41, 1978.

There are, however, two major drawbacks to the use of *E. coli* capsular antigens as human vaccines. First approximately 40% of *E. coli* bacteremic isolates cannot be serotyped as relates to capsular antigen. In addition, the K1 and K5 capsular antigens, which are expressed by more than 20% of K-typeable blood isolates, are poorly immunogenic in humans due to their antigenic cross-reactivity with mammalian glycosaminoglycans. Therefore, a K antigen-based *E. coli* vaccine would have a limited coverage, and hence, little utility.

Based upon the above finding, a serospecific LPS-based vaccine would appear to possess the greatest potential to protect against *E. coli* extraintestinal infections. Native LPS, however, is far too toxic and pyrogenic for use as a human vaccine. The O serospecificity of *E. coli* is contained within the O-polysaccharide (O-PS) moiety of the LPS molecule as for other gram-negative bacteria. The O-PS region can be separated from the toxic lipid A portion of the LPS molecule by cleavage in dilute acetic acid followed by pelleting of the insoluble lipid A moiety by centrifugation. While O-PS isolated in this manner is serologically reactive nontoxic and non pyrogenic, it is non-immunogenic due to its small molecular weight as noted in Pier, G. B., Sidberry, H. F., Sadoff, J. C., "Protective immunity induced in mice by immunization with high molecular polysaccharide from Pseudomonas aeruginosa," Infect. Immun. 22: 919-925, 1978; and Chester, I. R., Meadow, P. M., Pitt, T. L., "The relationship between O-antigenic lipopolysaccharides and serological specificity in strains of Pseudomonas aeruginosa of different O-serotypes," J. General Microbiol. 78: 305-318, 1973.

One means by which to produce a protective immune response to isolated O-PS is to covalently couple it to a carrier protein, yielding a conjugate vaccine. *Escherichia coli* O18 O-PS has been covalently coupled to both cholera toxin and *Pseudomonas aeruginosa* toxin A, yielding safe, immunogenic, and protective monovalent conjugate vaccines as described in Cryz, S. J., Jr., Cross, A. S., Sadoff, J. C., Fürer, E., "Synthesis and characterization of *Escherichia coli* O18 )-polysaccharide conjugate vaccines," Infect. Immun. 58: 373-377, 1990; and Cryz, S. J., Jr., Cross, A. S., Sadoff, J. C., Wegmann, A., Que, J. U., Fürer, E., "Safety and immunogenicity of *Escherichia coli* O18 O-specific polysaccharide (O-PS)-toxin A and O-PS-cholera toxin conjugate vaccines in humans," J. Infect. Dis. 163: 1040-1045, 1991.

However, any vaccine against *E. coli* based on serospecific O-PS determinants would have to be multivalent based upon the observation that the majority (~70%) of bacteremic infections are caused by 10-12 different serotypes of *E. coli*. Serospecificity is conferred by both the monosaccharide composition of O-PS and the type of chemical linkage between each monosaccharide as noted in Ørskov, F., Ørskov, I., "Serotyping of *Escherichia coli*," Methods in Microbiology 14: 43-112, 1984. Therefore, the conditions used to synthesize the above described O18 monovalent conjugate might not be suitable for other serotypes of *E. coli*.

By the present invention, isolated O-PS from 12 serotypes of *E. coli* were covalently coupled to *P. aeruginosa* toxin A which serves as a "carrier protein" for the O-PS. The conditions employed to covalently couple toxin A to *E. coli* O-PS effectively detoxify the toxin A molecule and preserve the antigenicity of the O-PS moiety. The resulting polyvalent conjugate was found to be safe and immunogenic in humans when administered by the parenteral route.

SUMMARY OF THE INVENTION

Accordingly, it is an object of the present invention to provide a means of producing a polyvalent nontoxic vaccine against *E. coli* which is effective against the different *E. coli* serotypes.

It is another object of the present invention to provide monovalent O-PS-toxin A conjugates specific for various *E. coli* serotypes for use in a polyvalent vaccine.

In one embodiment, the present invention describes a method of producing a polyvalent nontoxic, immunogenic *E. coli* O-PS-toxin A conjugate vaccine. The method includes deriving O-PS from specific strains of *E. coli* shown to produce good levels of smooth LPS possessing complete O-PS regions; oxidizing the O-PS under strictly controlled conditions to produce reactive aldehyde groups; covalently introducing a spacer molecule into toxin A by the use of a water-soluble carbodiimide as a coupling agent; and contacting the toxin A-spacer molecule with oxidized polysaccharide to form monovalent nontoxic, immunogenic O-PS-toxin A conjugate vaccine.

In another embodiment, the present invention relates to a nontoxic, immunogenic E. coli vaccine formulated by combining monovalent O-PS-toxin A conjugate vaccines of differing serotypes to form a polyvalent vaccine.

In a further embodiment, the present invention relates to a conjugate comprising the O-polysaccharide region of an *E. coli* lipoplysaccharide molecule covalently coupled to a carrier protein.

Various other objects and advantages of the present invention will become apparent from the following description of the invention.

DETAILED DESCRIPTION OF THE INVENTION

The present invention relates to *E. coli*-protein conjugates for use in vaccines against *E. coli.* The present invention further relates to a method of producing such vaccines.

The novel method of the present invention produces a polyvalent nontoxic, immunogenic vaccine against *E. coli.* Utilizing the method of the present invention, monovalent serotype-specific conjugates are prepared and combined to yield a polyvalent vaccine. The immunogenic vaccine comprises conjugates of the present invention in an amount sufficient to elicit a humoral antibody response and a pharmaceutically acceptable carrier.

In the method of the present invention, the vaccine conjugates are prepared by isolating O-PS from *E. coli* strains which produce good levels of smooth LPS possessing complete O-PS regions. Suitable *E. coli* strains based upon seroepidemiological surveys include, but are not limited to, serotypes 01, 02, 04, 06, 07, 08, 012, 015, 016, 018, 025 and 075. The O-PS is isolated so as to be essentially free of lipid A and oxidized to produce reactive aldehyde groups. Preferably, 40 to 80% of the available reducing sugars of the O-PS are oxidized during the treatment. For example, the O-PS can be oxidized by exposure to $NaIO_4$, preferably for less than 5 minutes, more preferably for 2–5 minutes.

The conjugate is then formed by covalently coupling lipid A-free O-polysaccharide through at least one hydroxyl or carboxyl group to a carrier protein. Suitable carrier proteins for use in the present invention include, for example, toxin A, tetanus toxoid, cholera toxin, diphtheria toxoid, protein CRM 197 produced by *Corynebacterium diphtheriae,* outer membrane proteins from gram-negative bacteria, specifically group B *Neisseria meningitidis,* heat labile toxin of *Escherichia coli,* the B subunit from either cholera toxin or heat labile toxin of *E. coli* or bacterial heat-shock proteins. The carrier protein can be coupled directly to the O-PS or via a spacer molecule.

A prefered carrier protein is toxin A which is coupled to the purified O-PS by a spacer molecule, such as, adipic acid dihydrazide. The spacer molecule irreversibly detoxifies toxin A and as well as functioning as a bifunctional spacer molecule which can be bound to O-PS.

Polyvalent vaccines are produced by combining two or more monovalent conjugates prepared from O-PS of different serotypes as described above. For example, a polyvalent vaccine of the present invention can contain conjugates composed of O-PS from serotypes 02, 04, 06 and 018, or 02, 04, 06, 07, and 018, or 01, 02, 04, 06, 07, 08 and 018, or 01, 02, 04, 06, 07, 08, 012 and 018, or 01, 02, 04, 06, 07, 08, 012, 015 and 018, or 01, 02, 04, 06, 08, 012, 015, 016 or 018, or 01, 02, 04, 06, 07, 08, 012, 015, 016, 018 and 025, or 01, 02, 04, 06, 07, 08, 012, 015, 016, 018, 025 and 075.

Conjugates of the present invention, formed as described above, have a molecular weight of greater than 600,000. Unlike native LPS and toxin A, conjugates to the present invention are nontoxic. Moreover, unlike native LPS, the conjugates are nonpyrogenic. The conjugates of the present invention are immunogenic engendering an antibody response to both the O-PS and toxin A moieties.

The following non-limiting examples are provided to further illustrate the present invention. In generating the data included herein, the *E. coli* strains listed below in Table 3 were used as the source of LPS. It is to be understood, however, that other strains of *E. coli* expressing the same serotypes may be used contingent upon their synthesizing a smooth LPS structure containing complete O-PS, though not necessarily with equivalent results.

Preparation of O-PS-Toxin A Conjugates

Nontoxic, immunogenic conjugates of the present invention were synthesized by covalently linking O-PS containing serospecific determinants derived from hydrolyzed *E. coli* LPS to toxin A. Adipic acid dihydrazide (ADH) was used as a spacer molecule. The covalent linking of ADH to toxin A results in the complete destruction of the adenosine diphosphate ribose-transferase activity which renders toxin A nontoxic as described in Cryz, S. J., Jr., Fürer, E., Sadoff, J. C., Germanier, R., "Pseudomonas aeruginosa immunotype 5 polysaccharide-toxin A conjugate vaccine," Infect. Immun. 52: 161–165, 1986. Conjugates synthesized in this manner from O-PS derived from LPS of the 12 most common serotypes of *E. coli* associated with sepsis possessed a molecular weight of greater than 600,000, were nontoxic, nonpyrogenic, and immunogenic. Antibody engendered by this vaccine in both rabbits and humans was protective against experimental *E. coli* infections when passively transferred to mice. Vaccination elicited both an anti-*E. coli* LPS and an antitoxin A IgG antibody response.

By the method of the present invention, LPS was isolated and purified as described by Cryz, S. J., Jr, Cross, A. S., Sadoff, J. C., Fürer, E., "Synthesis and characterization of *Escherichia coli* O18 O-polysaccharide conjugate vaccines," Infect. Immun. 58: 373–377, 1990. LPS prepared in this manner contained less than 2% (wt/wt) protein and nucleic acids. O-PS containing serospecific antigenic determinants was derived from purified LPS by mild acid hydrolysis. Purified LPS (1 g) was suspended in 200 ml of a 1% (vol/vol) acetic acid in water solution. The solution was placed in a round bottle fitted with a reflux-cooler and boiled for 90 minutes in a hemispherical flask heater. After cooling, the insoluble lipid A was pelleted by centrifugation and discarded. The supernatant was neutralized with 0.2 N NaOH and filter-sterilized through a 45 μm filter to remove traces of lipid A. The solution was concentrated by rotary evaporation under reduced pressure. The concentrate was passed through a 5×40 cm G-25 column (Pharmacia Fine Chemicals, Uppsala, Sweden) equilibrated in distilled water. The fractions were collected and analyzed for carbohydrate content using the phenol-sulfuric acid method as described by Westphal, O., Luderitz, O., Bister, F., "Ueber die Extraction von Bakterien mit Phenol-Wasser," Z. Naturforsch [B] 7: 148-155, 1952. The carbohydrate containing fractions (M, ≦70,000) were pooled, concentrated by rotary evaporation, sterilized through passage through a 0.22 μm filter, and lyophilized. The lyophilized material was analyzed for pyrogenicity in rabbits at an intravenous dose of 10 μg per kilogram body weight. Only pyrogen-free material was used to prepare the conjugates.

Toxin A was purified as described in Cryz, S. J., Jr, Fürer, E., Germanier, R., "Protection against P. aeruginosa infection in a murine burn wound sepsis model by passive transfer of antitoxin A, antielastase and antilipopolysaccharide," Infect. Immun. 39: 1072-1079, 1983, except that the production strain was a spontaneously isolated hyperproducer of toxin A derived from P. aeruginosa strain PA103, termed PA103-FeR. The final purified preparations consisted of greater than 95% toxin A protein as determined by high pressure liquid chromatography.

The O-PS was next oxidized to generate reactive aldehyde groups as follows. Lyophilized O-PS (60 mg) was reconstituted in 12 ml of distilled water. Solid NaIO$_4$ (258 mg; E. Merck and Co., Darmstadt, Germany) was added and the reaction allowed to proceed for 2 minutes. The oxidation reaction was stopped by the addition of ethylene glycol (0.12 ml). The length of time that the O-PS was exposed to NaIO$_4$ during the oxidation process was found to be critical as concerns the immunogenicity of the oxidized O-PS upon coupling to toxin A. Conjugates constructed of O-PS oxidized for more than 5 minutes were found to be reduced in immunogenicity as shown below in Table 1. This trend was consistent for all 3 serotypes of O-PS studied and appeared to be related to the extent to which the O-PS was oxidized. This finding indicates that critical epitopes expressed by E. coli O-PS are readily destroyed by excessive oxidation. This was an unexpected finding over Cryz, S. J., Fürer, E. P., "Nontoxic Pseudomonas aeruginosa polysaccharide-tetanus toxoid and polysaccharide-toxin A conjugate vaccines," U.S. Pat. No. 4,771,127, 10/88, where it was shown that the O-PS from P. aeruginosa could be oxidized in the presence of NaIO$_4$ for 2 hours and still yield a highly immunogenic conjugate when coupled to a suitable carrier protein. Table 1 shows the effect of different oxidation times on the immunogenicity of O-PS conjugate vaccines.

TABLE 1

Effect of the Extent of Oxidation Time on the Immunogenicity of O-PS Conjugates

| O-PS serotype | Oxidation Time (min.) | Degree of Oxidation (%) | Immunogenicity[1] [Mean IgG ELISA Titer (range)] | |
|---|---|---|---|---|
| O18 | 2 | 65 | 71 | (18-244) |
|  | 5 | 78 | 44 | (18-201) |
|  | 10 | 83 | 23 | (18-33) |
| O4 | 5 | ND[2] | 67 | (51-90) |
|  | 10 | ND | 8.3 | (0-48) |
| O6 | 2 | ND | 61 | (32-100) |
|  | 10 | ND | 10 | (6-24) |
|  | 60 | ND | 0 | |

[1]Rabbits (3 per group) were immunized on days 0 and 14 with an amount of conjugate equal to 50 μg of O-PS.
[2]ND = not done.

The mixture was concentrated by rotary evaporation under reduced pressure and the oxidized O-PS was separated from other reactants by filtration over Sephadex G-25 (Pharmacia Fine Chemicals, Uppsala, Sweden). Column fractions were collected and monitored for carbohydrate content by the phenol-sulfuric acid method described in Dubois, M., Gilles, K. A., Hamilton, J. K., Rebers, P. A., Smith, F., "Colorimetric method for determination of sugars and related substances," Anal. Chem. 28: 350-356, 1956. The fractions containing oxidized O-PS were pooled and lyophilized.

Adipic acid dihydrazide (ADH) was utilized for two purposes: (i) to irreversibly detoxify toxin A following its covalent coupling to the toxin A molecule; and (ii) to act as a spacer molecule by virtue of its 2 reactive groups, one of which is bound to toxin A, the other of which is available to combine with OPS. ADH was covalently coupled to toxin A as follows. Solid ADH (300 mg; Fluka AG, Buchs, Switzerland) and 1-ethyl-3(-3-dimethylaminopropyl) carbodiimide (30 mg; Sigma Chemical Co., St. Louis, Mo.) were added to 150 mg of toxin A (5 mg/ml in 0.05 M Na$_2$HPO$_4$-NaH$_2$PO$_4$, pH 7.2). The solution was stirred for 2 hours at 22° C. during which time the pH of the solution was maintained at 4.8 by the addition of 0.3 N HCl using a pH-stat (Methrom, Herisan, Switzerland). The toxin A-ADH solution was then extensively dialyzed against 0.05 M phosphate buffered saline, pH 7.2 (PBS). The solution was centrifuged at 5,000×g for 10 minutes to remove any insoluble material.

Toxin A-ADH was coupled to oxidized O-PS as follows. The toxin A-ADH solution was diluted in 50 mM phosphate buffer, pH 7.0, at a final concentration of 2 mg/ml. An equal amount of oxidized O-PS was added and the mixture incubated for 1 hour at 22° C. NaCNBH$_3$ was added to a final concentration of 20 mM and the solution incubated an additional 72-96 hours at 22° C. This mixture was extensively dialyzed against PBS containing 0.02% Merthiolate (PBS-M) and applied to a Sephadex G-100 column equilibrated in PBS-M. The column was eluted with PBS-M and the conjugate-containing void volume fractions collected and stored at 4° C.

The final polyvalent vaccine was produced as follows. The 12 monovalent conjugates were combined and mixed under aseptic conditions in such a manner that the final solution contained 50 μg of each polysaccharide serotype per ml (equal to 600 μg/ml). This mixture was then dialyzed against 10 volumes of half-strength PBS containing 5% (wt/vol) lactose and 0.01% Merthiolate. The mixture was aseptically with-drawn from the dialysis bag, and 1 ml was placed into 3-ml sterile glass vials. The vials were capped, and lyophilized under aseptic conditions. The caps were fitted in situ, sealed with aluminum caps, and the vials labeled.

Characteristics of O-PS-Toxin A Conjugate vaccine various physicochemical, safety, and immunogenic characteristics of the O-PS-toxin A conjugate vaccines are shown in Tables 1–8. In specific regard to Table 1, the immunogenicity of the conjugates were found to be dependent upon the time over which the O-PS was exposed to $NaIO_4$ as part of the oxidation step to generate reactive aldehyde groups, essential for subsequent conjugate formation. The length of exposure to $NaIO_4$ affects the degree to which the O-PS is oxidized. For three different serotypes of O-PS, it was shown that exposure to $NaIO_4$ longer than 5 minutes at ambient temperature, which results in $\geq 80\%$ of sugars residues being oxidized, resulted in poorly immunogenic conjugates upon coupling to a carrier protein. Conjugates formulated with O-PS oxidized for 2 to 5 minutes yielded conjugates which were more immunogenic.

Various characteristics (molecular weight, toxicity, pyrogenicity, and immunogenicity) of LPS, O-PS, toxin A, and O-PS-toxin A conjugates are shown below in Table 2. The conjugates possessed a molecular weight greater than 600,000, which exceeded the molecular weight of their respective starting constituents, i.e. O-PS ($\leq 70,000$) and toxin A ($\sim 66,000$). LPS and toxin A were toxic for mice in their native forms. For example, the mean lethal dose for native toxin A when injected intraperitoneally was 0.2 µg/mouse. However, the covalent coupling of toxin A to O-PS resulted in a marked reduction in toxicity evidenced by the fact that there was no indication of toxicity when mice received the equivalent of 200 µg of toxin A protein as conjugate. Therefore, the methods used to construct the conjugate vaccines resulted in at least a 1,000-fold reduction in the toxicity of toxin A, in effect yielding a toxin A toxoid.

Native LPS was pyrogenic when administered intravenously at a dose of 0.1 µg/kg rabbit body weight. In contrast, both the purified O-PS and O-PS-toxin A conjugates were nonpyrogenic when administered at a dose of $\geq 10$ µg/kg. Due to its highly toxic nature, native toxin A was not assayed for pyrogenicity. Unconjugated O-PS was non-immunogenic when injected intramuscularly into rabbits. In contrast, all 12 monovalent O-PS-toxin A conjugate vaccines as well as the 12-valent conjugate vaccine were able to induce an immune response to each O-PS serotype and to toxin A.

TABLE 2

Characteristics of LPS, O-PS, Toxin A, and O-PS-Toxin A Conjugate Vaccine

| | LPS | O-PS | Toxin A | O-PS-Toxin A Conjugate Vaccine |
|---|---|---|---|---|
| Molecular weight[1] | $>10 \times 10^6$ | $<70,000$ | 66,000 | $>600,000$ |
| Toxicity[2] | $<1$ µg | Nontoxic ($>500$ µg) | 0.2 µg | Nontoxic ($>500$ µg) |
| Pyrogenicity[3] | $<0.1$ µg | $>10$ µg | ND[4] | $>10$ µg |
| Immunogenicity[5] | ND | Non-immunogenic | Immunogenic | Immunogenic |

[1]Determined by high pressure liquid chromatography using a Dupont Zorbax GF-250 column.
[2]Expressed as mean lethal dose following intraperitoneal injection into 18–20 g mice. For LPS experiments, mice were first sensitized with galactoseamine. Nontoxic signifies that a minimum of 500 µg of antigen administered intraperitoneally resulted in no mortality.
[3]The dose of antigen, expressed in µg/kg body weight, which when injected into rabbits by the intravenous route, resulted in a $\geq 0.3°$ C. increase in body temperature.
[4]ND = not done.
[5]Determined by immunizing groups of rabbits with 10 to 50 µg of each antigen. Sera were analyzed for the presence of specific IgG antibody by ELISA.

In summary, the data presented in Table 1 shows that the O-PS-toxin A conjugate vaccines were of a high molecular weight, nontoxic, nonpyrogenic, and able to induce a specific antibody response to both the O-PS and toxin A conjugate components.

The strains which provided the LPS from which the O-PS were isolated are shown in Table 3. These 12 serotypes were selected based upon seroepidemiological studies showing *E. coli* expressing these serotypes to be frequently associated with bacteremic episodes. These particular strains were selected based upon their ability to produce a substantial amount of smooth LPS possessing complete O-PS sidechains as determined by analysis of the LPS by sodium dodecylsulfate polyacrylamide gel electrophoresis followed by silver staining to visualize the bands. Other strains expressing these characteristics may be used although not necessarily with the same results.

TABLE 3

E. coli Strains Used for Isolation of LPS and O-PS

| Strain designation | Serotype | Source |
|---|---|---|
| 204 | O1 | A. Brauner Karolinska Hospital Stockholm, Sweden |
| 171 | O2 | A. Brauner Karolinska Hospital Stockholm, Sweden |
| 47 | O4 | Walter Reed Army Institute of Research, Washington, D.C. |
| 133 | O6 | A. Brauner Karolinska Hospital Stockholm, Sweden |
| EC10 | O7 | Walter Reed Army Institute of Research, Washington, D.C. |
| 208 | O8 | A. Brauner Karolinska Hospital Stockholm, Sweden |
| 253 | O12 | Walter Reed Army Institute of Research, Washington, D.C. |
| 11 | O15 | A. Brauner Karolinska Hospital Stockholm, Sweden |
| 104 | O16 | A. Brauner Karolinska Hospital Stockholm, Sweden |
| 205 | O18 | Walter Reed Army Institute of Research, Washington, D.C. |
| 60 | O25 | A. Brauner Karolinska Hospital Stockholm, Sweden |
| 3 | O75 | A. Brauner Karolinska Hospital |

TABLE 3-continued

E. coli Strains Used for Isolation of LPS and O-PS

| Strain designation | Serotype | Source |
|---|---|---|
| | | Stockholm, Sweden |

The composition of the 12 monovalent O-PS-toxin A conjugate vaccines (that is the ratio of O-PS and toxin A) prepared from O-PS of differing serotypes is shown below in Table 4. These monovalent conjugates were combined to form the polyvalent vaccine. The conjugates were composed of between 33.4% to 54.7% O-PS and 46.3% to 66.6% toxin A. Therefore, while the relative ratio of O-PS to toxin A may vary from serotype to serotype, it is preferable that each conjugate contains a minimum of 30% O-PS by weight.

TABLE 4

Composition of Monovalent Conjugates Used to Formulate the 12-Valent E. Coli O-PS-Toxin A Conjugate Vaccine

| Serotype | Conjugate Composition (%) | |
|---|---|---|
| | O-PS | Toxin A |
| O1 | 44.7 | 55.3 |
| O2 | 41.6 | 58.4 |
| O4 | 49 | 51 |
| O6 | 46.2 | 53.8 |
| O7 | 33.4 | 66.6 |
| O8 | 44.3 | 56.7 |
| O12 | 38.2 | 61.8 |
| O15 | 46 | 54 |
| O16 | 54.7 | 46.3 |
| O18 | 37 | 53 |
| O25 | 45.5 | 54.5 |
| O75 | 48.4 | 51.6 |

The ability of the polyvalent conjugate vaccine to elicit an immunoglobin G (IgG) antibody response in rabbits to each of the 12 LPS serotypes and to toxin A is shown below in Table 5. Immunization engendered at a 4-fold rise in mean IgG ELISA titer to all 13 vaccine antigens (12 LPS serotypes plus toxin A).

TABLE 5

Immunoglobulin G (IgG) Antibody Response Following Immunization with the 12-Valent E. coli O-PS-Toxin A Conjugate Vaccine

| Serotype | Mean IgG ELISA Titer (Range) | |
|---|---|---|
| | Pre-immune (Day 0) | Post-immune (Day 28) |
| O1 | 1.8 (1.3–3.2) | 88 (58–129) |
| O2 | 6.3 (4.4–10) | 252 (204–284) |
| O4 | 1.9 (1–3.6) | 46 (39–53) |
| O6 | 1.5 (0.6–9.7) | 111 (102–117) |
| O7 | 6.5 (4–11.1) | 268 (170–388) |
| O8 | 9.1 (2.7–24) | 447 (235–827) |
| O12 | 24 (9–45) | 1436 (1119–1782) |
| O15 | 4.7 (3–8) | 182 (100–271) |
| O16 | 11 (6.4–25) | 66 (55–85) |
| O18 | 5.9 (4.4–9.7) | 259 (192–352) |
| O25 | 4.7 (3–6.9) | 120 (59–166) |
| O75 | 2.5 (1.8–4.7) | 23 (14–42) |
| Toxin A | 14 (8.9–24) | 412 (351–512) |

Rabbits (3) were immunized on days 0 and 14 with an amount of vaccine equal to 25 μg of O-PS from each of the 12 serotypes.

The ability of passively transferred IgG antibody isolated from the serum of rabbits immunized with the polyvalent O-PS-toxin A vaccine to protect mice against fatal experimental E. coli sepsis caused by infection with the 12 serotypes of E. coli is shown in Table 6. Passively administered IgG, which contained elevated antibody titers to all 8 serotypes expressed by the challenge strains, significantly decreased the mortality rate when compared to the control groups, which received only buffer.

TABLE 6

Protection Against Experimental E. coli Sepsis by Passive Transfer of Rabbit Immune IgG

| Serotype of challenge strain | % Mortality | |
|---|---|---|
| | PBS | Immunge IgG |
| O1 | 100 | 60 |
| O2 | 100 | 0 |
| O4 | 60 | 0 |
| O6 | 100 | 20 |
| O7 | 80 | 0 |
| O8 | 100 | 0 |
| O15 | 60 | 20 |
| O18 | 100 | 0 |

Approximately 3 mg of IgG purified from the sera of rabbits immunized with the 12-valent E. coli O-PS-toxin A conjugate vaccine were administered intraperitoneally (IP) to mice about 3 to 5 hours prior to IP challenge with E. coli.

Safety and Immunogenicity of the Polyvalent O-PS-Toxin A vaccine in Humans

A polyvalent vaccine was prepared by combining 12 sterile monovalent conjugates composed of O-PS isolated from strains listed in Table 3 coupled to toxin A. Tests for sterility, pyrogenicity, and general safety were performed according to the procedures detailed in the United States Code of Federal Regulations 21.610. The polyvalent conjugate vaccine used for this example was composed of 43% O-PS and 57% toxin A. It was non-pyrogenic when administered intravenously to rabbits at a dose of 12 μg/kg body weight. There were no mortalities nor any sign of overt toxicity when 0.5 ml and 5.0 ml of reconstituted vaccine were administered intraperitoneally to mice and guinea pigs, respectively. The vaccine was stable to toxic reversion. Therefore, the intraperitoneal administration of 100 μg of toxin A protein as conjugate per mouse, which had previously been reconstituted and stored at 37° C. for 28 days, caused no overt signs of toxicity.

Healthy adult volunteers received a total of 698 μg of conjugate (equal to 300 μg of total O-PS [25 μg O-PS/serotype] and 398 μg of toxin A) in 0.5 ml administered intramuscularly in the deltoid area. All reactions subsequent to vaccination were recorded by the volunteer on a control sheet. Venous blood samples were drawn just prior to vaccination and at 28 days post-vaccination. The sera were collected as described in Cryz, S. J., Jr., Cross, A. S., Sadoff, J. C., Wegmann, A., Que, J. U., Fürer, E., "Safety and immunogenicity of Escherichia coli O18 O-specific polysaccharide (O-PS)-toxin A and O-PS-cholera toxin conjugate vaccines in humans," J Infect. Dis 163: 1040–1045, 1991.

Reactions to vaccination are detailed below in Table 7. Most (85%) of the vaccinees noted mild pain at the injection site while swelling and redness were reported by 30% and 20% of subjects, respectively. Only 3 subjects reported a systemic reaction, which consisted of headache (1) and malaise (2). No reactions hindered normal activities and all resolved spontaneously within 24–72 hours.

TABLE 7

Reactions Following Vaccination with *E. coli* O-PS-Toxin A Polyvalent Vaccine

| Local Reactions (%) | | | Sytemic Reactions (%) | | | |
|---|---|---|---|---|---|---|
| Pain | Swelling | Redness | Fever | Chills | Malaise | Headache |
| 85 | 30 | 20 | 0 | 0 | 10 | 5 |

Twenty healthy volunteers received a single dose of the vaccine containing 25 µg O-PS per vaccine serotype intramuscularly.

Immunization with the polyvalent O-PS-toxin A conjugate vaccine resulted in a substantial rise in mean anti-LPS IgG values to 11 of the 12 serotypes, the exception being serotype 016 (1.4-fold rise)as shown below in Table 8. The mean-fold rises ranged from 2.8-fold (012) to 20-fold (06). It is important to note that a far more vigorous response was noted in subjects whose baseline anti-LPS IgG levels were $\leq 10$ µg/ml. This type of "epitopic suppression" by high levels (210 µg/ml) of specific preexisting antibodies has been widely reported in the literature.

TABLE 8

Immunoglobulin G (IgG) Antibody Response Following Immunization of Humans with *E. coli* O-PS-Toxin A Polyvalent Vaccine

| | Geometric Mean µg IgG/ml Serum (Range) | | Mean-Fold Rise |
|---|---|---|---|
| Serotype | Day 0 | Day 28 | |
| O1 | 11 (1.4–55) | 38 (14–137) | 3.5 |
| O2 | 11 (2–53) | 36 (15–204) | 3.3 |
| O4 | 22 (6–71) | 50 (10–234) | 2.3 |
| O6 | 5 (0.5–77) | 98 (20–485) | 20 |
| O7 | 2.4 (0.6–20) | 25 (2–162) | 10 |
| O8 | 2 (0.7–15) | 20 (4–69) | 10 |
| O12 | 12 (2–40) | 33 (6–117) | 2.8 |
| O15 | 2.5 (0.6–19) | 12 (4–55) | 5 |
| O16 | 16 (2.4–58) | 22 (6–71) | 1.4 |
| O18 | 17 (2–78) | 68 (8–232) | 4 |
| O25 | 3 (0.4–56) | 8 (1–75) | 2.7 |
| O75 | 11 (0.5–63) | 47 (4–254) | 4.3 |
| Toxin A | 1 (0.4–34) | 5 (0.6–39) | 5 |

Volunteers received a single dose containing 25 µg of O-PS from each of the 12 vaccine serotypes on day 0.

While a preferred embodiment of the invention have been described herein, it will be obvious to those skilled in the art that various changes and modifications, especially pertaining to vaccine formulation as related to the number of serotypes of O-PS incorporated, may be made without departing from the spirit of the invention as defined in the following claims.

All publications given hereinabove are hereby incorporated by reference.

What is claimed is:

1. A method of preparing a polyvalent *E. coli* vaccine comprising the steps of:
   (i) preparing monovalent vaccines from each of the O-polysaccharide serotypes 01, 02, 04, 06, 07, 08, 012, 015, 016, 018, 025 and 075 by a process comprising the steps of:
   (a) purifying lipopolysaccharide from *E. coli* expressing complete O-polysaccharide side chains;
   (b) isolating the O-polysaccharide region of the lipopolysaccharide molecule resulting from step (a) by hydrolysis in dilute acid and purifying said O-polysaccharide essentially free of lipid A;
   (c) oxidizing reducing sugars of the O-polysaccharide with NaIO$_4$ for from 2–5 minutes and under conditions such that antigenicity is retained and reactive aldehyde groups are produced;
   (d) isolating the oxidized O-polysaccharide resulting from step (c);
   (e) covalently coupling said isolated oxidized O-polysaccharide resulting from step (d) via a hydroxyl or carboxyl group of said oxidized O-polysaccharide to a carrier protein; and
   (ii) combining the twelve monovalent vaccines of different serotypes resulting from steps (a)–(e) whereby said polyvalent vaccine is produced.

2. The method according to claim 1 wherein said oxidation is effected under conditions such that 40–80% of the available sugars of the O-polysaccharide are oxidized.

3. The method according to claim 1 wherein said carrier protein is toxin A.

4. The method according to claim 3 further comprising coupling said toxin A to a spacer molecule, which spacer molecule is then covalently coupled to said oxidized O-polysaccharide resulting from step (c) via at least one hydroxyl or carboxyl group of said O-polysaccharide.

5. The method according to claim 4 wherein said spacer molecule is adipic acid dihydrazide.

6. A method of preparing a polyvalent *E. coli* vaccine comprising the steps of:
   (i) preparing monovalent vaccines from each of the O-polysaccharide serotypes 01, 02, 04, 06, 07, 08, 012, 015, 016, 018, 025 and 0.75 by a process comprising the steps of:
   (a) purifying lipopolysaccharide from *E. coli* expressing compete O-polysaccharide side chains;
   (b) isolating the O-polysaccharide region of the lipopolysaccharide molecule resulting from step (a) by hydrolysis in dilute acid and purifying said O-polysaccharide essentially free of lipid A;
   (c) oxidizing reducing sugars of the O-polysaccharide with NaIO$_4$ for from 2–5 minutes and under conditions such that antigenicity is retained and reactive aldehyde groups are produced;
   (d) isolating the oxidized O-polysaccharide resulting from step (c);
   (e) covalently coupling adipic acid dihydrazide (ADA) to toxin A under conditions such that said toxin A is detoxified whereby toxin A-ADH is formed;
   (f) covalently coupling said toxin A-ADH to said oxidized O-polysaccharide resulting from step (d) via a hydroxyl or carboxyl group of said oxidized O-polysaccharide so that a conjugate is formed containing a minimum of 30% by weight of O-polysaccharide;
   (ii) combining the twelve monovalent vaccines of different serotypes resulting from steps (a)–(f) whereby said polyvalent vaccine is produced.

7. A polyvalent vaccine prepared by the method of claim 1.

* * * * *